United States Patent [19]

Wächtler et al.

[11] Patent Number: 5,204,476

[45] Date of Patent: Apr. 20, 1993

[54] FLUOROPHENYLPYRIDINES

[75] Inventors: Andreas Wächtler, Griesheim; Eike Poetsch, Mühltal; Thomas Geelhaar, Mainz; Reinhard Hittich, Modautal; Volker Reiffenrath, Rossdorf; Hans-Michael Kompter, Riedstadt-Erfelden, all of Fed. Rep. of Germany

[73] Assignee: Merck Patent Gesellschaft mit beschrankger Haftung, Fed. Rep. of Germany

[21] Appl. No.: 628,887

[22] Filed: Dec. 18, 1990

[30] Foreign Application Priority Data

Dec. 19, 1989 [DE] Fed. Rep. of Germany ....... 3941761
Jun. 20, 1990 [DE] Fed. Rep. of Germany ....... 4019595

[51] Int. Cl.⁵ .................. C07D 213/65; C07D 213/26; C07D 213/55; C07D 213/80
[52] U.S. Cl. .................................. 546/290; 546/302; 546/346; 546/341; 546/339
[58] Field of Search ............... 546/298, 300, 301, 302, 546/339, 290, 341, 346

[56] References Cited

U.S. PATENT DOCUMENTS

| | | | |
|---|---|---|---|
| 4,772,416 | 9/1988 | Goto | 546/339 |
| 4,834,904 | 5/1989 | Krause | 546/261 |
| 4,865,763 | 9/1989 | Inoue | 546/339 |
| 4,876,026 | 10/1989 | Saito | 544/315 |
| 4,913,837 | 4/1990 | Gray | 546/290 |
| 5,021,191 | 6/1991 | Saito | 252/299.6 |
| 5,032,312 | 7/1991 | Kelly | 544/239 |

Primary Examiner—C. Warren Ivy
Assistant Examiner—P. G. Spivack
Attorney, Agent, or Firm—Millen, White, Zelano & Branigan

[57] ABSTRACT

The invention relates to fluorophenylpyridines of the formula I:

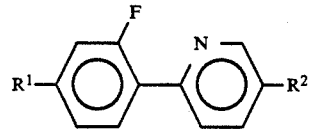

where
$R^1$ and $R^2$ are substituted and unsubstituted monovalent organic radicals.

4 Claims, No Drawings

FLUOROPHENYLPYRIDINES

BACKGROUND OF THE INVENTION

Chiral tilted smectic liquid-crystalline phases having ferroelectric properties can be prepared by adding one or more tilted smectic phases containing a suitable chiral additive to basic mixtures (L. A. Beresnev et al., Mol. Cryst. Liq. Cryst. 89, 327 (1982); H. R. Brand et al., J. Physique 44 (lett.), L 771 (1983). Such phases can be used as dielectrics for fast switching displays which are based on the principle of SSFLC technology, described by Clark and Lagerwall (N. A. Clark and S. T. Lagerwall, Appl. Phys. Lett. 36, 899 (1980); U.S. Pat. No. 4,367,924), based on the ferroelectric properties of the chiral tilted phase. In this phase, the elongated molecules are arranged in layers, the molecules having an angle of tilt with respect to the layer normal. On progressing from layer to layer, the direction of tilt changes by a small angle with reference to an axis perpendicular to the layers, with the result that a helical structure is formed. In displays based on the principle of SSFLC technology, the smectic layers are arranged perpendicularly to the plates of the cell. The helix-like arrangement of the directions of tilt of the molecules is suppressed by a very small spacing of the plates (approximately 1-2 μm). This forces the long axes of the molecules to arrange themselves in a plane parallel to the plates of the cell, as a result of which two distinct tilt orientations are produced By applying a suitable electrical alternating field it is possible to switch back and forth between these two states in the liquid-crystalline phase, which has a spontaneous polarization. This switching operation is substantially faster than in conventional twisted cells (TN LCDs) based on nematic liquid crystals.

A great disadvantage for many applications of the currently available materials having chiral tilted smectic phases (such as, for example, $S_C^*$, but also $S_h^*$, $S_I^*$, $S_J^*$, $S_K^*$, $S_G^*$, $S_F^*$) is their low chemical and thermal stability and low photostability. A further disadvantageous property of displays based on currently available chiral tilted smectic mixtures is that the spontaneous polarization has unduly low values, with the result that the switching time behavior of the displays is unfavorably affected and/or the pitch and/or the tilt and/or the viscosity of the phases does not meet the requirements of display technology. In addition, the temperature range of the ferroelectric phases is unduly small and is predominantly at unduly high temperatures.

SUMMARY OF THE INVENTION

The invention relates to fluorophenylpyridines of the formula I:

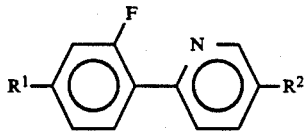

where
$R^1$ and $R^2$ are, in each case independently of each other, an unsubstituted alkyl or alkenyl radical or an alkyl or alkenyl radical substituted by CN or by at least one halogen and is preferably monohalogenated, dihalogenated or perfluorinated, which radical contains up to 18 carbon atoms and in which radical one or more $CH_2$ groups, preferably one or two, may be replaced by a radical selected from the group comprising —O—, —CO—O—, —O—CO—or —C≡C—, two oxygen atoms not being adjacent, one of the radicals $R^1$ and $R^2$ may also be a group of the formula II:

in which
$R^3$ is an unsubstituted alkyl, alkenyl or alkoxy group or an alkyl, alkenyl or alkoxy group substituted by CN or by at least one halogen, which group contains up to 18 carbon atoms,

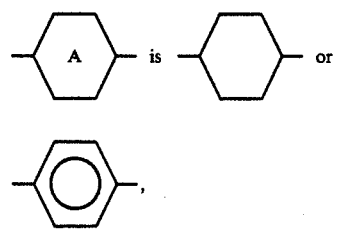

$Q^1$ is —CO—O—, —O—CO—, —CH$_2$O—, —OCH$_2$—, —CH$_2$CH$_2$—or a single bond, and
m is 1 or 2.

It has now been found that the use of compounds of the formula I as components of chiral tilted smectic mixtures can substantially reduce the disadvantages mentioned. The compounds of the formula I are consequently eminently suitable as components of chiral tilted smectic liquid-crystalline phases. In particular, it is possible to use them to prepare chiral tilted smectic liquid-crystalline phases which are particularly stable chemically and have beneficial ferroelectric phase ranges, beneficial ranges for the viscosity, in particular wide $S_C^*$ phase ranges, outstanding supercooling capability down to temperatures below 0° C. without crystallization occurring and spontaneous polarization values which are high for such phases. P is the spontaneous polarization in nC/Cm$^2$. The compounds of the formula I are, however, also suitable for liquid-crystalline phases for the electroclinic effect described by S. Garoff and R. B. Meyer in Physical Review Letters, 38, Nov. 15, 1977, pp. 848-851.

The compounds of the formula I have a neutral anisotropy of the relative permittivities (Δε= —0.1 to +0.5) and therefore have a wide field of application. Depending on the choice of the substituents, these compounds may be used as basic materials of which liquid-crystalline smectic phases are predominantly composed; however, compounds of the formula I may also be added to liquid-crystalline basic materials selected from other compound classes in order to vary, for example, the dielectric and/or optical anisotropy and/or the viscosity and/or the spontaneous polarization and/or the phase ranges and/or the angle of tilt and/or the pitch of such a dielectric.

EP 0,252,961 specifies a very wide general formula for nematic fluorophenylpyridines which encompasses some of the compounds of the formula I. In EP 0,252,961 there are no references of any kind to $S_c$ compounds of this type, it being intended, on the contrary, to suppress the smectic phases in particular. No individual compounds of the formula claimed here are mentioned therein either.

Chiral dopants for ferroelectric mixtures are claimed in EP-A-0,220,297 and EP-A-0,233,706 whose wide general formulae encompass the compounds according to the invention. In the compounds mentioned therein, however, the lateral halogen substituent on the phenyl ring is always in the meta position with respect to the pyridine ring. However, these have a positive $\Delta\epsilon$ and are therefore less suitable for ferroelectric mixtures.

EP 0,244,939 describes similar compounds of the formula

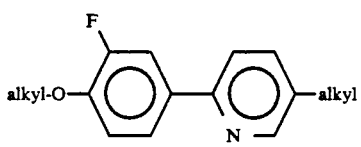

but these likewise have a positive $\Delta\epsilon$.

WO 87-04158 describes similar compounds of the formula

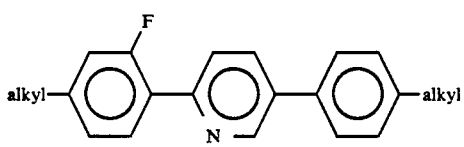

The person skilled in the art was consequently not able either to infer from the prior art in a simple manner synthesis possibilities for the compounds claimed or to perceive that the compounds according to the invention have predominantly wide and beneficially situated $S_C$ phases and are also distinguished by beneficial values for the rotational viscosity.

The invention consequently relates to the fluorophenylpyridines of the formula I, in particular of the formulae I1, I2 and I3, in which n and o are each 0 or 1 and m and p are each 1 to 18.

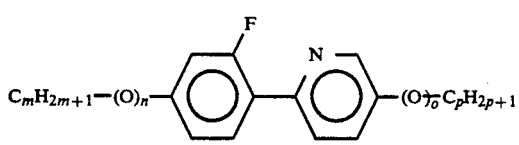

I1

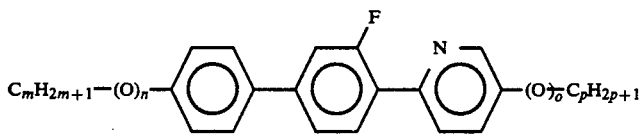

I2

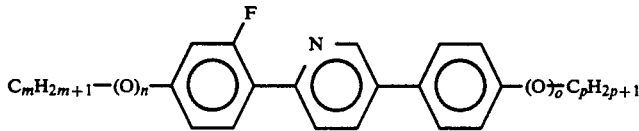

I3

The invention relates, in particular, to those optically active fluorophenylpyridines of the formula I in which one of the radicals $R^1$ and $R^2$ is a chiral group of the formula III:

III where
$R^4$ is a group of the formula

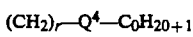

$(CH_2)_r—Q^4—C_oH_{2o+1}$ in which
$Q^4$ is —O—, —O—CO— or a single bond,
r is 0, 1 or 2, and
O is 1 to 7,
Y is CN, halogen or $CH_3$,
Z is a single bond or $—(CH_2)_p—$ in which one $CH_2$ group may be replaced by —O—, —O—CO— or —CO—O— and p is 1, 2, 3, 4, 5 or 6, and
$R^°$ is H or $CH_3$,
with the proviso that $R^°$ is different from Y.

The invention further relates to ferroelectric liquid-crystalline phases having a content of at least one compound of the formula I and also to liquid-crystal display components, in particular ferroelectric electro-optical display components, which contain such phases.

The phases according to the invention contain preferably at least two, and in particular, at least three compounds of the formula I. Particularly preferred are chiral tilted smectic liquid-crystalline phases according to the invention whose achiral basic mixture contains, in addition to compounds of the formula I, at least one other component having negative dielectric anisotropy or positive dielectric anisotropy which is small in magnitude. This further component or these further components of the achiral basic mixture may form 1 to 50%, preferably 10 to 25%, of the basic mixture. Suitable further components having positive or negative dielectric anisotropy which is small in magnitude are compounds of the formula IV which encompasses compounds of the subformulae IVa to IVi:

IVa

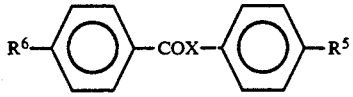

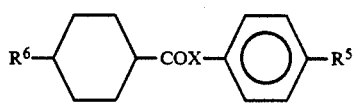
IVb

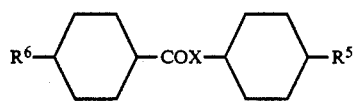
IVc

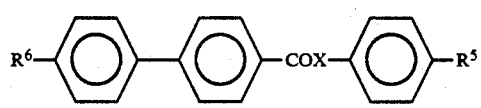
IVd

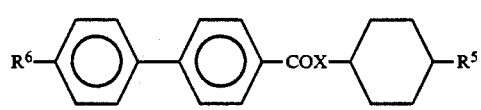
IVe

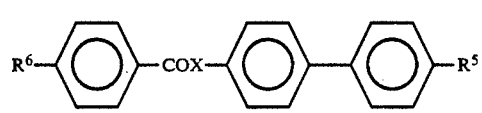
IVf

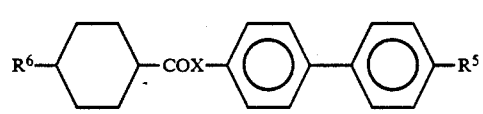
IVg

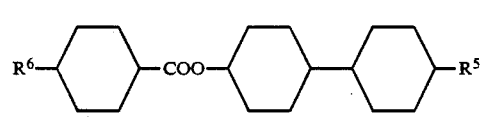
IVh

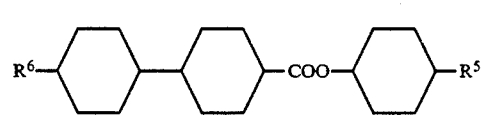
IVi $R^6$ and $R^5$ are in each case alkyl containing 1 to 15 carbon atoms in which a $CH_2$ group may also be replaced by —O—, —CO—O— or —O—CO—, preferably straight-chain alkyl, alkoxy, alkanoyloxy or alkoxycarbonyl containing in each case 3 to 12 carbon atoms. X is oxygen or sulfur, preferably oxygen. In the compounds of the formulae IVa, IVb, IVd, IVe, IVf and IVg, a 1,4-phenylene group may also be laterally substituted by halogen or CN, in particular, preferably by fluorine.

Particularly preferred are the compounds of the subformulae IVa, IVb, IVd and IVf in which $R^6$ and $R^5$ are in each case straight-chain alkyl or alkoxy containing in each case 5 to 10 carbon atoms.

Particularly preferred individual compounds are specified in Table I below:

TABLE I

| Formula | $R^6$ | $R^5$ | X |
|---|---|---|---|
| IVa | n-decyloxy | n-heptyloxy | O |
| IVa | n-hexyloxy | n-decyloxy | O |
| IVa | n-octyloxy | n-heptyl | O |
| IVa | n-octyloxy | n-pentyl | O |
| IVa | n-decyloxy | n-heptyl | O |
| IVa | n-decyloxy | n-pentyl | O |
| IVf | n-pentyl | n-pentyl | O |
| IVf | n-pentyl | n-hexyl | O |

The compounds of the subformulae IVc, IVh and IVi are suitable as additives for lowering the melting point and are normally added to the basic mixtures in an amount of not more than 5%, preferably 1 to 3%. $R^6$ and $R^5$ in the compounds of the subformulae IVc, IVh and IV i are preferably straight-chain alkyl containing 2 to 7, preferably 3 to 5, carbon atoms. A further class of compound which is suitable for lowering the melting point int he phases according to the invention is that of the formula:

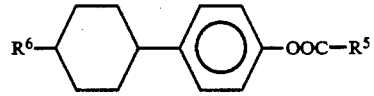

in which $R^6$ and $R^5$ have the preferred meaning specified for IVc, IVh and IVi.

Further suitable components having negative dielectric anisotropy are furthermore compounds containing the structural element A, B or C.

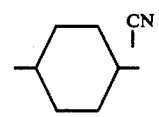 A

 B

 C

Preferred compounds of this type correspond to the formulae Va, Vb and Vc:

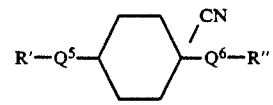

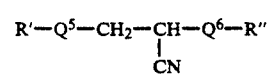

R' and R'' are in each case alkyl containing 1 to 15 carbon atoms, in which a $CH_2$ group may also be replaced by —O—, preferably straight-chain alkyl or alkoxy groups containing in each case 2 to 10 carbon atoms. $Q^5$ and $Q^6$ are in each case 1,4-phenylene, trans-1,4-cyclohexylene, 4,4'-biphenylyl, 4-trans-4-cyclohexyl)phenyl, trans-4,4'-bicyclohexyl or one of the groups $Q^5$ and $Q^6$ is also a single bond.

$Q^7$ and $Q^8$ are in each case 1,4-phenylene, 4,4'-biphenylyl or trans-1,4-cyclohexylene. One of the groups $Q^7$ and $Q^8$ may also be 1,4-phenylene in which at least one CH group is replaced by N. R''' is an optically active radical, preferably an n-alkyl or alkoxy radical containing 3 to 12 carbon atoms containing an asymmetric carbon atom of the structure

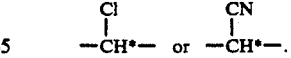

Particularly preferred compounds of the formula Vc are those of the formula Vc':

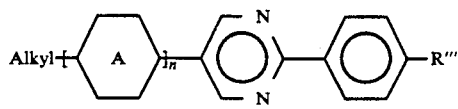
Vc' in which A is 1,4phenylene or trans-1,4-cyclohexylene and n is 0 or 1.

Particularly preferred are those ferroelectric liquid-crystalline phases having a content of at least one achiral fluorophenylpyridine of the formula Ia, at least one achiral phenylpyrimidine of the formula Vc' in which R''' is an alkyl or alkoxy radical containing up to 18 carbon atoms as basic material having a wide $S_C$ phase and at least one chiral fluorophenylpyridine of the formula I as optically active dopant. Those ferroelectric liquid-crystalline phases are furthermore preferred which contain, in addition to the specified compounds of the formula I1 and Vc and one chiral compound of the formula I, at least one phenylpyridine of the formula Vd and/or a 2,3-difluorophenylpyrimidine of the formula Ve and/or a phenylpyrimidine of the formula Vf and/or Vg:

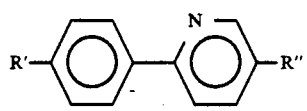
Vd

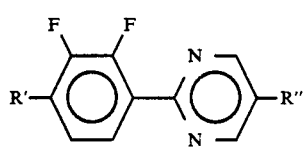
Ve

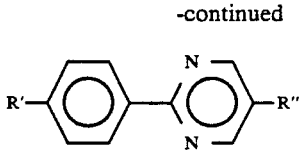
Vf

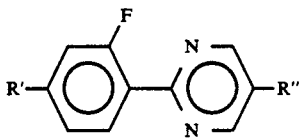
Vg

The nonchiral fluorophenylpyridines of the formula I4

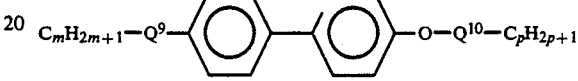
I4 in which m and p are, in each case independently of each other, 1 to 18, $Q^9$ is —O— or a single bond and $Q^{10}$ is —CO—, —CO—, —CH$_2$— or a single bond, are particularly suitable as components of smectic basic materials.

The compounds of the formula I4 encompass the nonchiral preferred binuclear and trinuclear materials of the formulae Ia to If listed below, in which m and p are in each case independently 1 to 18.

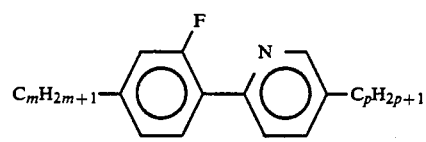
Ia

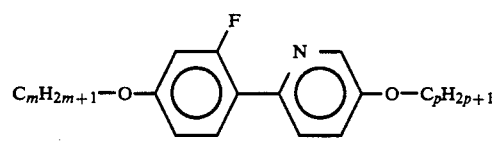
Ib

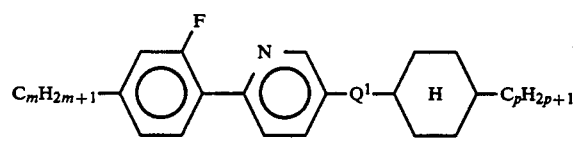
Ic

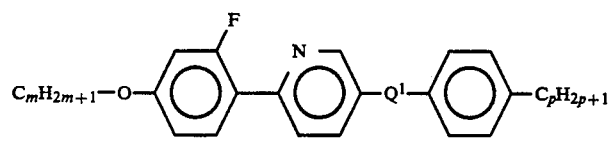
Id

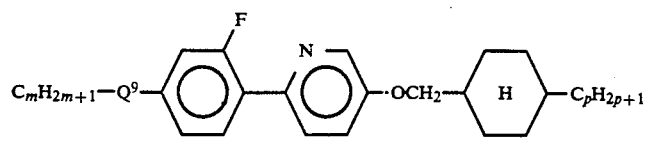
Ie

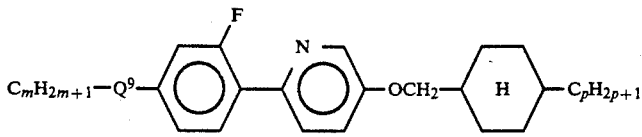

The compounds of the formulae I2 and I3 encompass the nonchiral preferred compounds of the formulae Ig to Ij listed below, in which m and p are 1 to 18 in each case.

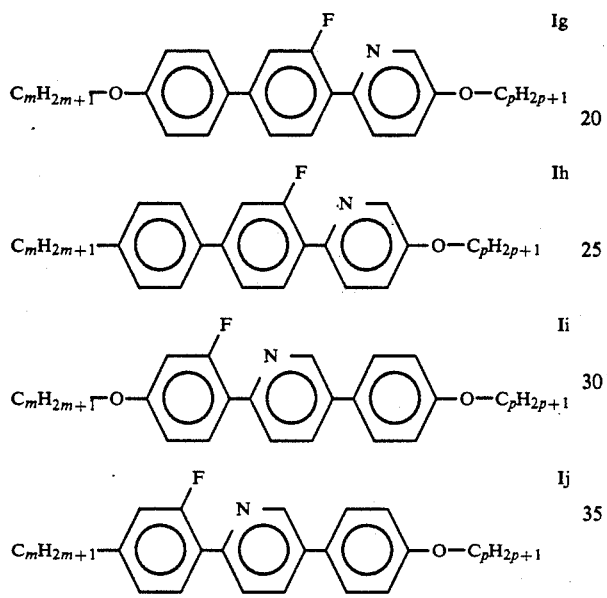

Among these, those of the subformulae Ia and Ib are particularly preferred.

m is preferably 5 to 14, in particular 6 to 12. p is preferably 3 to 12. The radicals $C_mH_{2m+1}$ and $C_pH_{2p+1}$ are preferably straight-chain. Compounds of the formula I having relatively short radicals of this type, wherein the sum of m+p is 2 to 9, preferably 4 to 7, are also suitable as components of nematic phases.

The chiral fluoropyridines of the formula I in which one of the radicals $R^1$ and $R^2$ is a group of the formula III are outstandingly suitable as dopants for inducing ferroelectricity in a smectic basic material. They are distinguished, in particular, by a high spontaneous polarization of more than 2, preferably more than 5, in particular more than 10 nC/cm$^{-1}$.

Furthermore, they do not destabilize the smectic phase of these basic materials. The radicals of the formula III is denoted below by R*.

The chiral compounds of the formula I accordingly encompass the compounds of the subformulae Ik to In containing 2 rings, in which m and p are 1 to 18 in each case and o and r are 0 or 1 in each case:

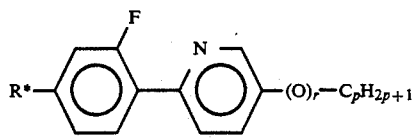

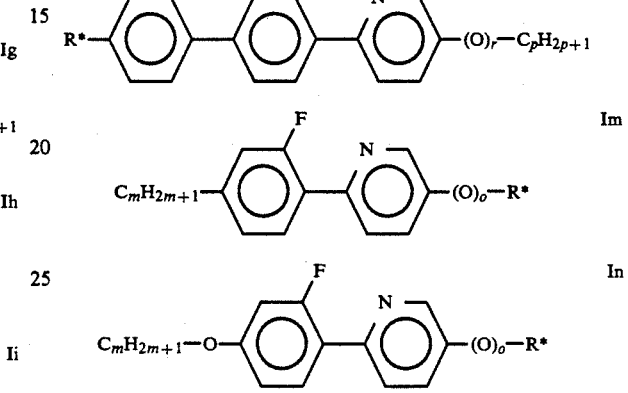

and also the compounds of the formulae Io to Iw containing 3 rings:

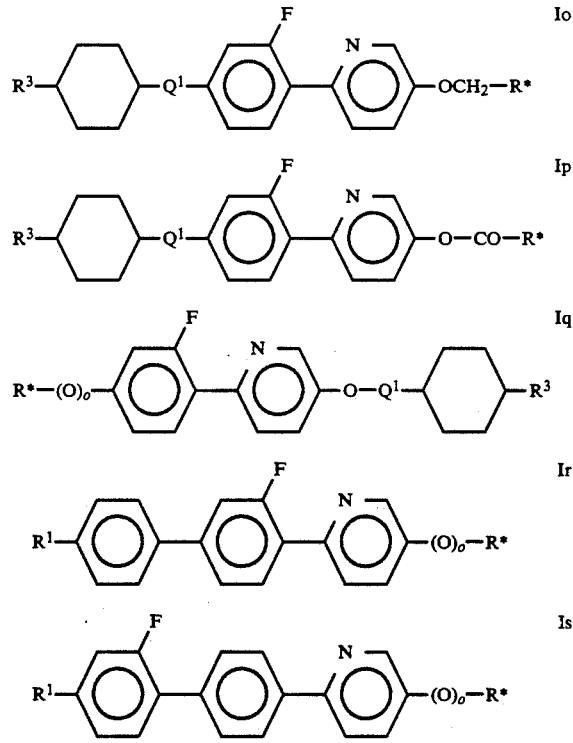

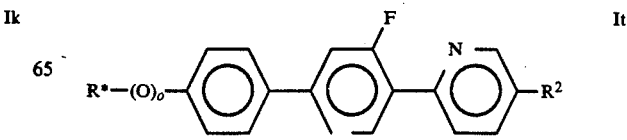

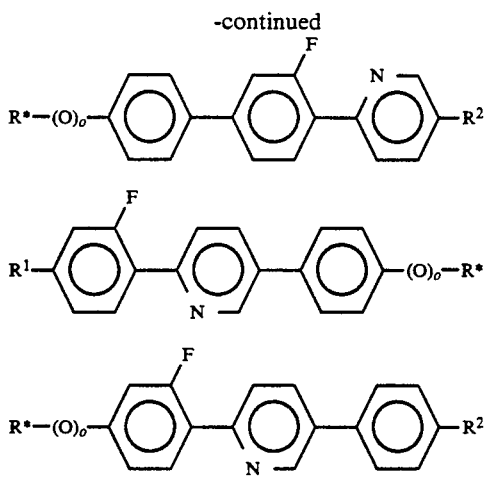

in which m and n have the preferred meanings specified for the compounds of the formulae Ia to Ih.

Preferred in particular are those of the subformulae Ik and Io.

Among these, those chiral compounds of the formula I are particularly preferred in which R* is a chiral monofluorinated group of the formula IIIa;

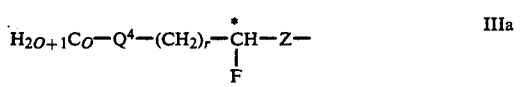

in which O and $Q^4$ have the specified meaning, r is 1 or 2 and Z is —$CH_2$—, —O—, —$CH_2O$—, —O—CO, —CO—O or a single bond.

The chiral radicals of the formula IIIa accordingly encompass the chiral monofluoroalkyl, monofluorooxaalkyl and alkanoyloxymonofluoroalkyl group $R_f^*$ of the formulae IIIa1 to IIIa6, in which O and r have the specified meaning and n is 0 or 1:

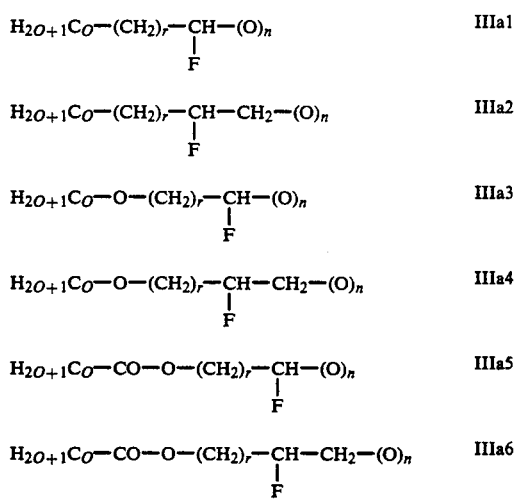

Of the chiral monofluoro groups $R_f^*$ of the formulae IIIa1 to IIIa6, those of the formulae IIIa1, IIIa3 and IIIa5 are particularly preferred, in particular those in which r is 2.

Those chiral compounds of the formula I are furthermore preferred in which the chiral group R* of the formula III is a group of the formula IIIb

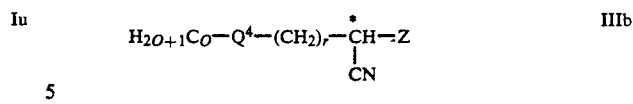

in which O and $Q^4$ have the specified meaning, r is 1 or 2 and Z is —$CH_2$—, —$CH_2O$—, —O—, —CO—O—, —O—CO—or a single bond.

The compounds of the formula I are prepared by methods known per se such as those described in the literature (for example in the standard works such as Houben-Weyl, Methoden der Organischen Chemie (Methods of Organic Chemistry), Georg-Thieme-Verlag, Stuttgart).

The starting substances may, if desired, also be formed in situ so that they are not isolated from the reaction mixture but are immediately converted further to form the compounds of the formula I.

The compounds according to the invention can easily be prepared by the following reaction schemes (scheme 1 to scheme 4).

Scheme 1

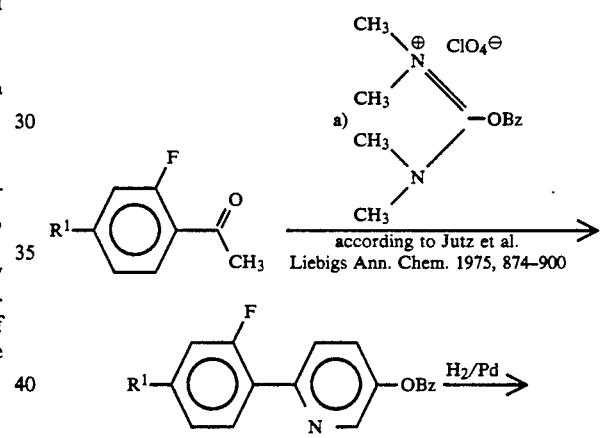

Scheme 2

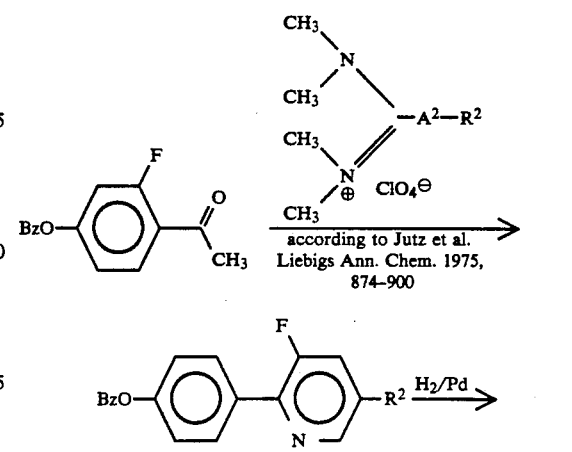

-continued

The compounds according to the invention are furthermore obtainable by coupling organometallic zinc compounds to appropriate bromopyridine derivatives according to DE-OS 3,632,410.

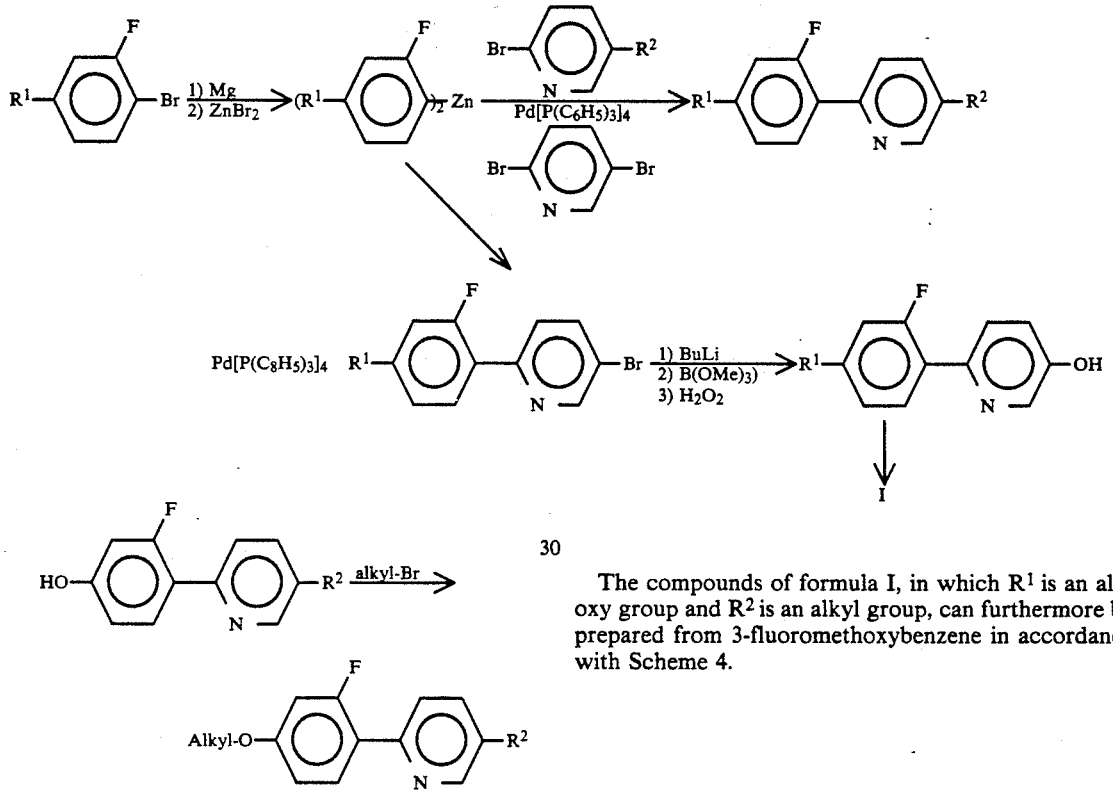

Scheme 3

The compounds of formula I, in which $R^1$ is an alkoxy group and $R^2$ is an alkyl group, can furthermore be prepared from 3-fluoromethoxybenzene in accordance with Scheme 4.

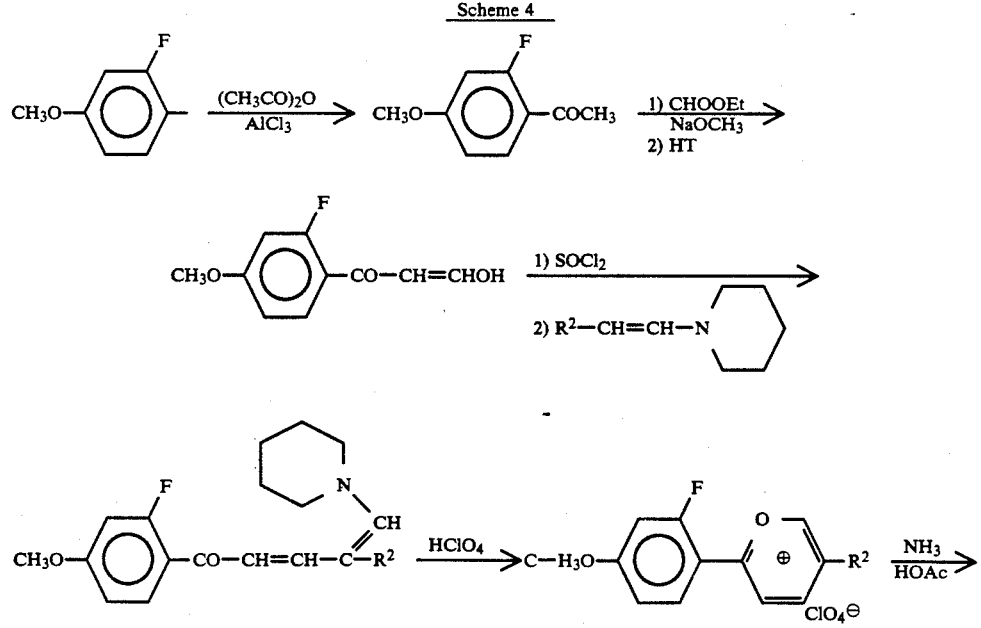

Scheme 4

-continued

Scheme 4

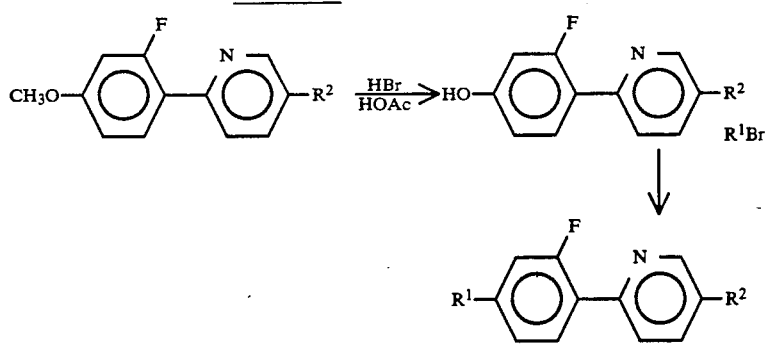

The benzyl group can be split off hydrogenolytically and the hydroxyl group then etherified or esterified again by known methods.

Scheme 5

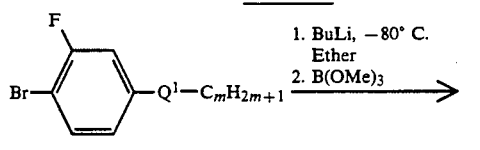

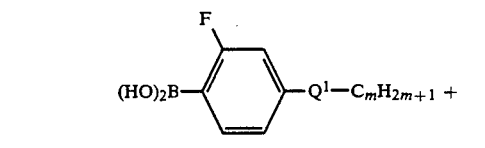

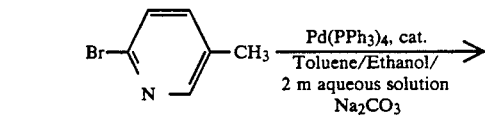

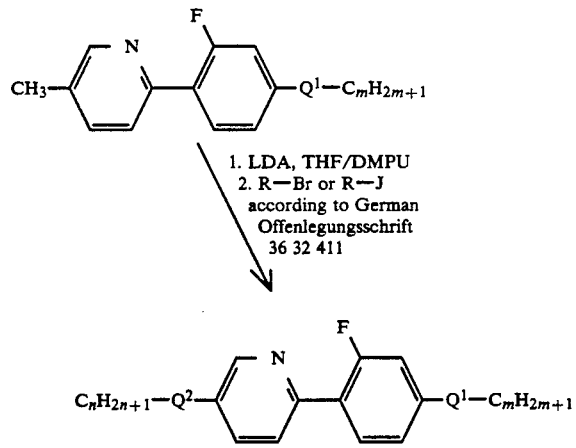

$Q^2 =$ 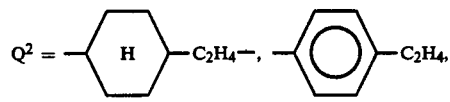

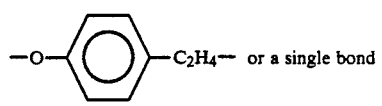 — or a single bond

The boronic acid necessary for the cross coupling according to Scheme 1 is also obtained by direct orthometallation according to

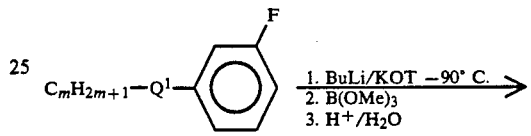

The synthesis of some particularly interesting hydroxy intermediate stages are described below:

a) 5-Hydroxy-2-(2-fluoro-4-alkylphenyl)pyridines or 5-hydroxy-2-(2-fluoro-4-alkoxyphenyl)pyridines can be obtained from 2-benzyloxytrimethinium salt by condensation with 4-alkyl- or 4-alkoxy-2-fluoroacetophenones, reaction with $NH_3/NH_4Cl$ or ammonium acetate analogously to the instructions of Ch. Jutz et al. (Liebigs Ann. Chem. 1975 874–900) and subsequent hydrogenolysis or from 4-alkyl- or 4-alkoxy-2-fluorophenylboronic acid respectively by coupling to 5-acetoxy-2-bromopyridine (obtainable from 5-hydroxy-2-bromopyridine by esterification) in the presence of a Pd catalyst in accordance with the papers by Suzuki et al. (Synth. Commun. 11 513-19 (1981)).

b) 5-Alkoxy-2-(2-fluoro-4-hydroxyphenyl)pyridines can be obtained by coupling 4-benzyloxy-2-fluorophenylboronic acid to 5-alkoxy-2-bromopyridine in accordance with the abovementioned literature and subsequent hydrogenolysis.

A further possibility in principle for preparing -(subst-phenyl)-5-alkoxypyridines is provided by the Cu-catalyzed bromine-alkoxy exchange in the appropriate 2-(subst-phenyl)-5-bromopyridines (obtainable by cross coupling 2,5-dibromopyridine to appropriately substituted ˉphenyl boronic acid under the Snieckus conditions) analogously to the procedures of H. L. Aalten (Tetrahedron 45 (17) 5565 (1989)) carried out using bromo benzene as an example and also a bromine-alkoxy exchange in the N-oxides of the appropriate 5-bromopyridines. The 5-alkoxypyridine N-oxides obtained by the last named means then have to be reduced to 5-alkoxypyridine by a method known from the literature.

The optically active compounds of the formula I can be prepared, in particular, in accordance with the reaction schemes below (Scheme I to Scheme IV).

Thus, to prepare compounds of the formula I* in which r=2, suitable precursors can be prepared from optically active malic acid by reaction scheme I below:

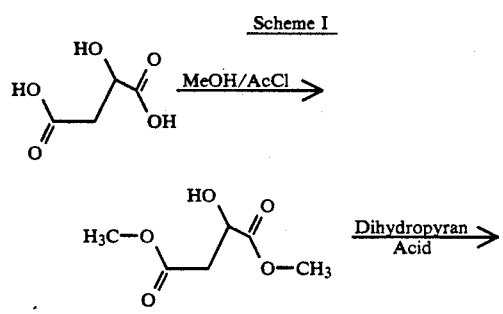

Up to this stage, the synthesis due to Mori et al has been described (K. Mori, T. Takigawa and T. Matsuo, Tetrahedron 35, 933-944 (1979)).

Later Meyers and Lawson then found that the chemical purity of the acetonide obtained in this way is only about 90% (A. I. Meyers and J. P. Lawson, THL 23 4883-4886 (1982)).

Regardless of this, the free alcohol group of the acetonide can be etherified by one of the usual methods (for example, C. A. Brown and D. Barton, Synthesis (1974) 434 or B. R. Jursic, Tetrahedron 44, 6677-6680 (1988)).

The benzyl ether (K. Isaac and P. Kocienski, J. Chem. Soc., Chem. Commun. (1982) 460-462) is suitable in particular as a protective group since it can be easily split off later hydrogenolytically. After the etherification, the isopropylidene ketal is hydrolyzed under standard conditions to the 1,2-diol and this can then be converted into the corresponding epoxide in accordance with the reaction conditions of Di Fabio and Misiti (R. Di Fabio and D. Misiti, Gazetta Chimica Italiana 118, 209-210 (1988)).

The treatment of the acetonide with HBr/glacial acetic acid and the subsequent reaction of the bromooxyalkyl acetates obtained in this manner with potassium pentanolate also yields, according to the work of U. Schmidt et al., the desired epoxides according to Scheme II (U. Schmidt, J. Tabiersky, F. Bartowiak and J. Wild, Angew. Chem. 92, 201-202 (1980)).

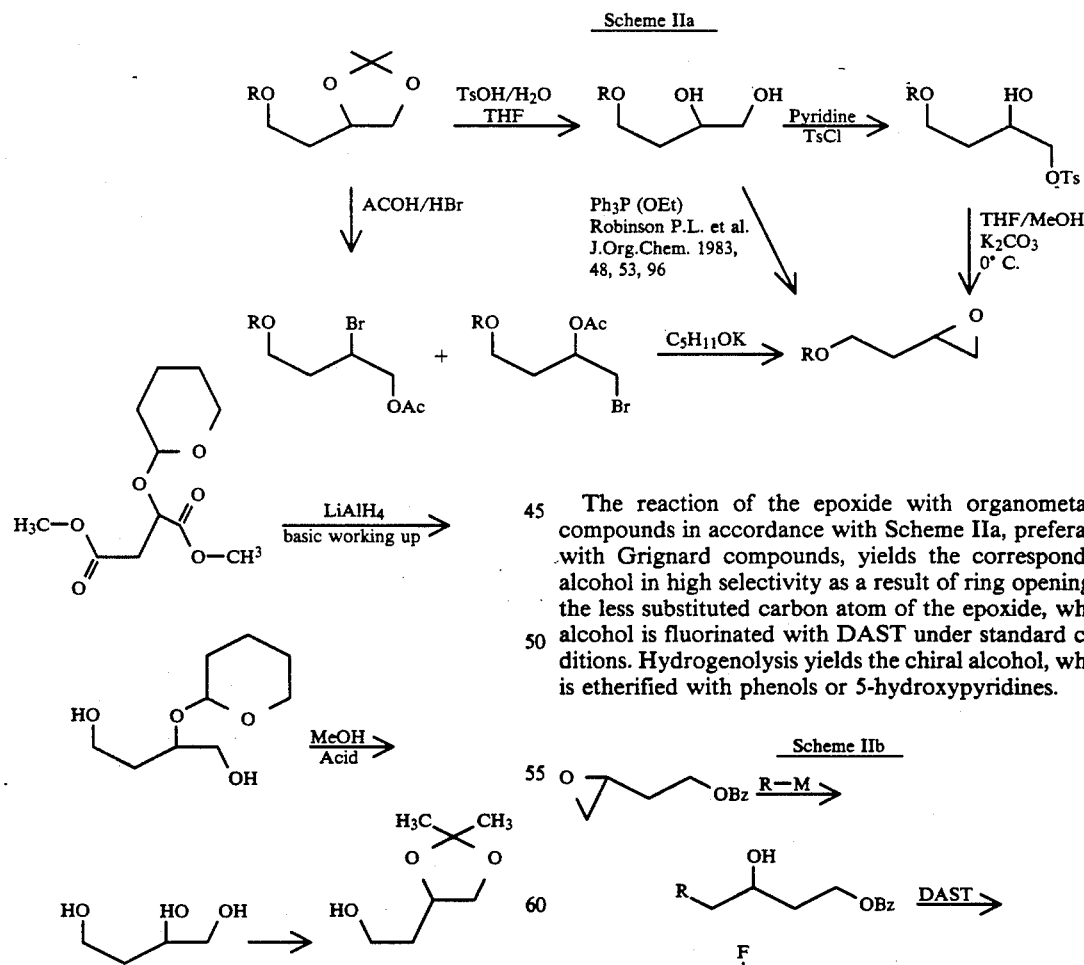

The reaction of the epoxide with organometallic compounds in accordance with Scheme IIa, preferably with Grignard compounds, yields the corresponding alcohol in high selectivity as a result of ring opening at the less substituted carbon atom of the epoxide, which alcohol is fluorinated with DAST under standard conditions. Hydrogenolysis yields the chiral alcohol, which is etherified with phenols or 5-hydroxypyridines.

If the epoxide is opened with pyridine/HF (N. Mongelli, F. Animati et al., Synthesis 310 (1988)), the corresponding fluoroalcohol is obtained which can then be converted into the corresponding tosylate. Such tosylates are suitable, in particular, for alkylating phenols and 5-hydroxypyridines in accordance with Scheme III or Scheme IV.

pounds according to the invention, this being accompanied by inversion. For the usual reactions of alcohols with DAST, see M. Hudlicky, Organic Reactions 35, 513-637 (1987).

The compounds according to the invention in which $Q^3 = $—O—CO— can be prepared from the corresponding benzyl ethers by hydrogenolysis and subsequent

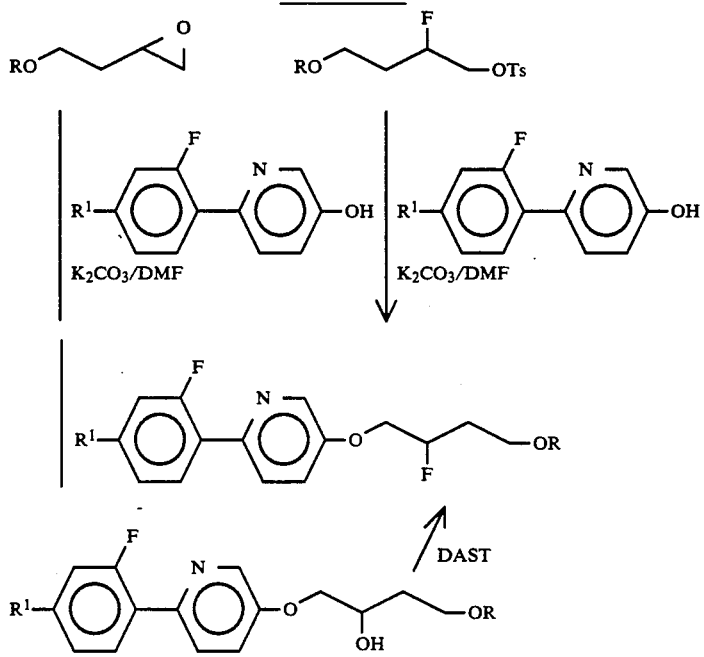

Scheme III

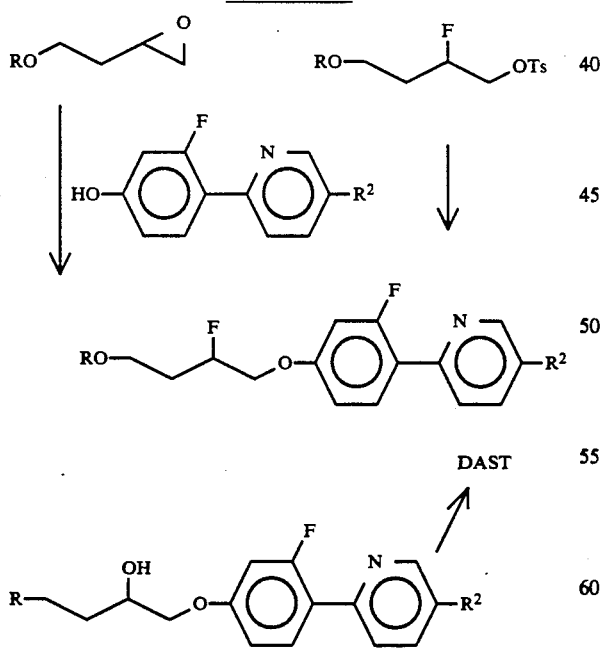

Scheme IV

As the above reaction schemes show, the epoxide may also be reacted directly with phenols. The epoxide is opened with high selectivity at the less substituted carbon atom to form the chiral secondary alcohol which is then converted with DAST into the compounds according to the invention esterification. The following synthesis scheme V describes the preparation:

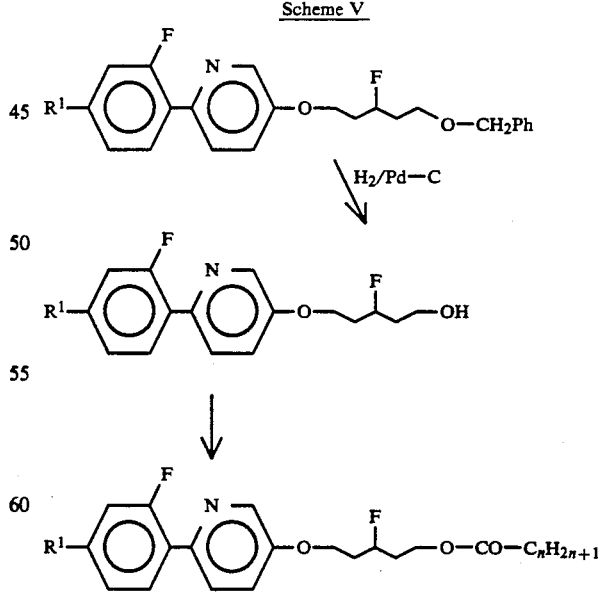

Scheme V

The compounds in which $Q^3 = $—O—CO— are furthermore obtained by oxidizing the corresponding fluoroalcohols and then esterifying with mesogenic phenols in accordance with Scheme VI:

Scheme VI

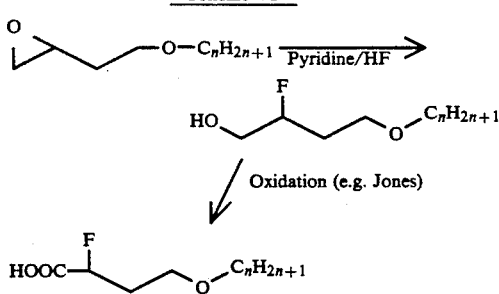

If a racemization occurs during the oxidation, the optically active fluoroacids can be obtained by Helmchen racemate resolution (Angew. Chem. 91, 65 (1979)).

The compounds of the formula I are also suitable as components of nematic liquid-crystalline phases, for example for avoiding reverse twist.

These liquid-crystalline phases according to the invention are composed of 2 to 25, preferably 3 to 15, components, including at least one compound of the formula I. The other components are preferably selected from the nematic or nematogenic substances, in particular the known substances from the classes comprising the azoxybenzenes, benzylideneanilines, biphenyls, terphenyls, phenylbenzoates or cyclohexylbenzoates, phenyl cyclohexanecarboxylates or cyclohexyl cyclohexanecarboxylates, phenylcyclohexanes, cyclohexylbiphenyls, cyclohexylcyclohexanes, cyclohexylnaphthalenes, 1,4-biscyclohexylbenzenes, 4,4'-biscyclohexylbiphenyls, phenylpyrimidines or cyclohexylpyrimidines, phenylpyridazines or cyclohexylpyridazines and also their N-oxides, phenylhexyldioxanes or cyclohexyldioxanes, phenyl-1,3-dithianes or cyclohexyl-1,3-dithianes, 1,2-diphenylethanes, 1,2-dicyclohexylethanes, 1-phenyl-2-cyclohexylethanes, optionally halogenated stilbenes, benzyl phenyl ethers, tolanes or substituted cinnamic acids.

The most important compounds which are suitable as components of such liquid-crystalline phases can be characterized by the formula I':

R'—L—G—E—R''     I' where L and E are each a carbocyclic or heterocyclic ring system composed of the group formed from 1,4-disubstituted benzene rings and cyclohexane rings, 4,4'-disubstituted biphenyl, phenylcyclohexane and cyclohexylcyclohexane systems, 2,5-disubstituted pyrimidine rings and 1,3-dioxane rings, 2,6-disubstituted naphthalene, di- and tetrahydronaphthalene, quinazoline and tetrahydroquinazoline,

| G is | —CH=CH— | —N(O)=N— |
|---|---|---|
| | —CH=CY— | —CH=N(O)— |
| | —C≡C— | —CH$_2$—CH$_2$— |
| | —CO—O— | —CH$_2$—O— |
| | —CO—S— | —CH$_2$—S— |
| | —CH=N— | —COO—Phe—COO— | or a C—C single bond,

Y is halogen, preferably chlorine, or —CN, and R' and R'' are alkyl, alkoxy, alkanoyloxy, alkoxycarbonyl or alkoxycarbonyloxy containing up to 18, preferably up to 8, carbon atoms, or one of these radicals is also CN, NC, NO$_2$, CF$_3$, F, Cl or Br.

In most of these compounds, R' and R'' are different from each other, one of these radicals usually being an alkyl group or alkoxy group. However, other variants of the substituents envisaged are also common. Many such substances or even mixtures thereof are obtainable commercially. All these substances are obtainable by methods known in the literature.

The phases according to the invention contain about 0.1 to 99, preferably 10 to 95%, of one or more compounds of the formula I. Liquid-crystalline phases according to the invention containing 0.1–40, preferably 0.5–30%, of one or more compounds of the formula I are furthermore preferred.

The phases according to the invention are prepared using methods which are standard per se. As a rule, the components are dissolved in one another, expediently at elevated temperature.

The liquid-crystalline phases according to the invention can be modified by suitable additives in such a way that they can be used in all the types of liquid-crystal display components hitherto known.

Such additives are known to the person skilled in the art and are described in detail in the literature. For example, conducting salts, preferably ethyldimethyldodecylammonium 4-hexyloxybenzoate, tetrabutylammonium tetraphenylboranate or complex salts of crown ethers (cf. for example, I. Haller et al., Mol. Cryst. Liq. Cryst. volume 24, pages 249-258 (1973)) may be added to improve the conductivity, pleochroic dyestuffs may be added to produce colored guest-host systems or substances may be added to alter the dielectric anisotropy, the viscosity and/or the orientation of the nematic phases.

Such substances are described, for example, in German Offenlegungsschrift 2,209,127, 2,240,864, 2,321,632, 2,338,281, 2,450,088, 2,637,430, 2,853,728 and 2,902,177.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding applications Federal Republic of Germany p 39 41 761.1, filed Dec. 19, 1989, and Federal Republic of Germany P 40 19 595.3, filed Jun. 20, 1990, are incorporated by reference.

"Standard working-up" means that water is added, extraction is carried out with methylene chloride, isolation is carried out, the organic phase is dried and evaporated down, and the product is purified by crystallization and/or chromatography.

Furthermore
C: denotes crystalline,
N: denotes nematic
S: denotes smectic
I: denotes isotropic.

The numbers appearing between these symbols specify the phase transition temperature in °C. in each case. The following abbreviations are furthermore used:
DAST: diethylaminosulfur trifluoride
DMF: dimethylformamide
n-BuLi: n-butyllithium

EXAMPLE 1

0.1 mol of 2-(4-nonyl-2-fluorophenyl)-5-hydroxypyridine (prepared by condensation of 4-nonyl-2-fluoroacetophenone with 2-benzyloxytrimethinium perchlorate in accordance with Jutz et al. (see page 17) with subsequent hydrogenolysis of the benzyl ether) is etherified with 0.11 mol of 1-bromoheptane and 0.11 mol of potassium carbonate in dimethylformamide as solvent. After working up, the 2-(4-nonyl-2-fluorophenyl)-5-heptyloxypyridine is recrystallized from isopropanol.

2-(4-Hydroxy-2-fluorophenyl)-5-octyloxypyridine, which is alkylated with 1-bromodecane to produce 2-(4-n-decyloxy-2-fluorophenyl)-5-octyloxypyridine, is obtained analogously by reacting 4-benzyloxy-2-fluoroacetophenone with 2-octyloxytrimethinium perchlorate, ammonium acetate 5. and hydrogenating cleavage of the benzyl ether.

The following compounds of the formula I4 are prepared analogously:

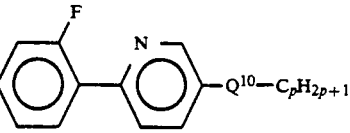

$C_mH_{2m+1}$—$Q^9$—[ring]—[ring-N]—$Q^{10}$—$C_pH_{2p+1}$

| m | $Q^9$ | $Q^{10}$ | p |
|---|---|---|---|
| 7 | 0 | 0 | 8 |
| 7 | 0 | 0 | 10 |
| 7 | — | 0 | 11 |
| 7 | — | 0 | 12 |
| 8 | 0 | 0 | 8 |
| 8 | 0 | 0 | 9 |
| 8 | — | 0 | 10 |
| 8 | — | 0 | 11 |
| 8 | — | 0 | 12 |
| 10 | — | 0 | 8 |
| 10 | — | 0 | 9 |
| 10 | 0 | 0 | 10 |
| 10 | 0 | 0 | 11 |
| 10 | 0 | 0 | 12 |
| 12 | — | 0 | 8 |
| 12 | — | 0 | 9 |
| 12 | 0 | 0 | 10 |
| 12 | 0 | 0 | 11 |
| 12 | 0 | 0 | 12 |
| 8 | — | OCH₂—[H]— | 3 |
| 8 | — | OCH₂—[H]— | 4 |
| 8 | 0 | OCH₂—[H]— | 5 |
| 8 | 0 | OCH₂—[H]— | 7 |
| 7 | 0 | OCH₂—[H]— | 3 |
| 7 | 0 | OCH₂—[H]— | 4 |
| 7 | — | OCH₂—[H]— | 5 |
| 7 | — | OCH₂—[H]— | 7 |
| 7 | — | OCH₂—[H]— | 8 |

The compounds of the formula I2 are obtained analogously from 2-(4'-alkyl-2-fluoro-4-biphenylyl)-5-hydroxypyridines (prepared from 4'-alkyloxy-4-acetyl-2-fluorobiphenyl in accordance with Example 1).

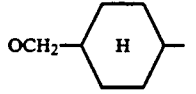

$C_mH_{2m+1}$—$(O)_n$—[ring]—[ring-F]—[ring-N]—O—$C_pH_{2p+1}$

| m | n | p |
|---|---|---|
| 8 | 1 | 7 |
| 8 | 1 | 8 |
| 5 | 0 | 7 |
| 9 | 1 | 6 |
| 9 | 1 | 7 |
| 9 | 1 | 8 |
| 9 | 1 | 9 |
| 4 | 1 | 5 |
| 3 | 0 | 7 |

The compounds of the formula I3 are obtained analogously from 4-[2-(4-alkoxy-2-fluorophenyl)pyridin-5-yl]phenols (prepared from 1'-alkoxy-4-acetyl-3'-fluorobenzene and 2-(4-benzyloxyphenyl)trimethinium perchlorate in accordance with Example 1).

The following esters of the formula I are obtained analogously:

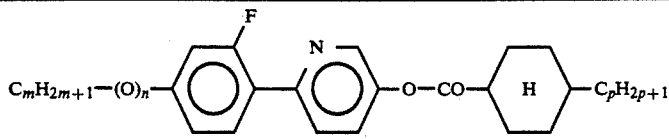

| m | n | p |
| --- | --- | --- |
| 8 | 1 | 3 |
| 8 | 1 | 5 |
| 8 | 1 | 7 |
| 8 | 1 | 9 |
| 8 | 1 | 10 |
| 8 | 1 | 11 |
| 8 | 0 | 3 |
| 8 | 1 | 5 |
| 10 | 0 | 3 |
| 7 | 1 | 7 |
| 7 | 1 | 11 |
| 7 | 0 | 3 |

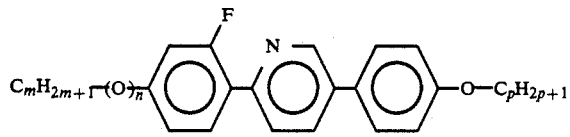

| m | n | p |
| --- | --- | --- |
| 8 | 1 | 7 |
| 8 | 1 | 8 |
| 6 | 1 | 6 |
| 5 | 0 | 3 |
| 5 | 0 | 7 |
| 9 | 1 | 6 |
| 9 | 1 | 7 |
| 9 | 1 | 8 |
| 9 | 1 | 9 |
| 4 | 1 | 5 |
| 3 | 0 | 7 |
| 11 | 1 | 6 |
| 6 | 1 | 11 |

EXAMPLE 2

0.1 mol of 2-(4-heptyloxy-2-fluorophenyl)-5-hydroxypyridine (prepared from 4-heptyloxy-2-fluoroacetophenone in accordance with Example 1) is dissolved together with 0.12 mol of pyridine in toluene and 0.1 mol of nonanoyl chloride is then added at room temperature. Stirring is then carried out for 12 hours and standard working-up is carried out. 2-(4-Heptyloxy-2-fluorophenyl)5-nonanoyloxypyridine is obtained.

EXAMPLE 3

A solution of 0.1 mol of 5-heptyloxy-2-(4-(2-hydroxy-5-oxaoctyloxy)-2-fluorophenyl)pyridine (prepared by heating optically active 1,2-epoxy-5-oxaoctane, obtainable from malic acid, with 5-heptyloxy-2-(4-hydroxy-2-fluorophenyl)pyridine in the presence of dry potassium carbonate and methyl ethyl ketone as solvent) in methylene chloride is cooled to −40° C. and 0.11 mol of DAST is added to it dropwise with moisture being excluded. The reaction mixture is then stirred for 12 hours while heating slowly to room temperature. Then hydrolysis is carried out with ice cooling and the reaction mixture is washed with dilute sodium hydroxide solution and several times with water. After drying over magnesium sulfate, the solvent is removed on a rotary evaporator and the crude product is purified chromatographically and - by crystallization. Optically active 5-heptyloxy-2-(4-(2-fluoro-5-oxaoctyloxy)-2-fluorophenyl)pyridine is obtained.

The following optically active compounds of the formula Ik are prepared analogously:

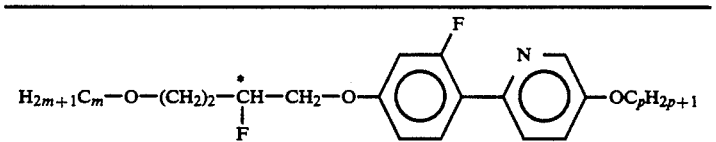

| m | p |
| --- | --- |
| 2 | 7 |
| 4 | 7 |
| 5 | 7 |
| 2 | 8 |
| 3 | 8 |
| 4 | 8 |
| 5 | 8 |
| 3 | 9 |
| 3 | 10 |

EXAMPLE 4

By analogy with Example 3, 2-(4-octyloxy-2-fluorophenyl)-5-(2-fluoro-5-oxyoctyloxy)pyridine is obtained from 0.1 mol of 2-(4-octyloxy-2-fluorophenyl)-5-hydroxypyridine (prepared in accordance with Example 1) and 0.1 mol of optically active 1,2-epoxy-5-octane. The following compounds of the formula In are prepared analogously:

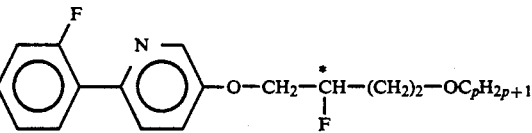

| m | p |
|---|---|
| 7 | 3 |
| 9 | 3 |
| 11 | 3 |

EXAMPLE 5

0.17 mol of diethyl azodicarboxylate (DEAD) dissolved in THF is added to a solution of 0.15 mol of 2-(4-decyloxy-2-fluorophenyl)-5-hydroxypyridine (prepared in accordance with Example 1), 0.17 mol of ethyl L(−)-lactate and 0.15 mol of triphenylphosphine in 400 ml of THF. In this process, a reaction temperature of 50° C. should not be exceeded. Stirring is carried out for 1 hour at 50° C. and then overnight at room temperature. Then the solvent is distilled off, the residue is dissolved in hot toluene and the solution is then slowly allowed to cool. The triphenylphosphine oxide precipitated is filtered off by suction, the filtrate is evaporated down and the residue is chromatographically purified. Ethyl 2-[2-(4-Decyloxy-2-fluorophenyl)pyridine-5-oxy]propionate ester is obtained.

EXAMPLE 6

Optically active benzyl lactate is etherified by means of diethyl azodicarboxylate (DEAD)/triphenylphosphine with 2-(4-octyloxy-2-fluorophenyl)-5-hydroxypyridine (prepared in accordance with Example 1) and the benzyl group is then split off hydrogenolytically. The acid so obtained is converted as usual into the nitrile (oxalyl chloride, ammonia, thionyl chloride). Optically active 2-(4-octyloxy-2-fluorophenyl)-5-(1-cyanoethoxy)-pyridine is obtained.

EXAMPLE 7

A solution of 0.1 mol of DCC in methylene chloride is added at 0° C. to a mixture of 0.1 mol of 2-(4-octyl-2-fluorophenyl)-5-hydroxypyridine (prepared in accordance with Example 1), 0.1 mol of optically active 2-chloro-3-methyl butyric acid (prepared from valine) and a catalytic amount of 4-(N,N-dimethylamino)pyridine in 250 ml of methylene chloride. Then the solution is allowed to stand for 12 hours at room temperature, the precipitate is filtered off by suction, the filtrate is worked up as standard and 2-(4-octyl-2-fluorophenyl)-5-pyridinyl 2-chloro-3-methylbutyrate is obtained.

EXAMPLE 8

Preparation of 2-(4-octyloxy-2-fluorophenyl)-5-methylpyridine 0.04 mol of 2-fluoro-4-octyloxyphenylboronic acid, 0.035 mol of 2-bromo-5-methylpyridine and 1.4 g of Pd(PPh₃)₄ as catalyst are boiled under reflux in a solvent mixture composed of 65 ml of toluene, 25 ml of ethanol and 40 ml of a 2 m Na₂CO₃ solution for 18 hours with atmospheric oxygen being excluded. Then working up is carried out as usual and the product is purified chromatographically and by crystallization.

Preparation of 2-(4-octyloxy-2-fluorophenyl)-5-nonylpyridine

With atmospheric oxygen and moisture being excluded, 7.9 mmol of 2-(4-octyloxy-2-fluorophenyl)-5-methylpyridine dissolved in THF and, about 15 minutes later, 8.7 mmol of 1-bromooctane are added at −70° C. to a solution of 8.7 mmol LDA (prepared from BuLi and diisopropylamine) in THF in the presence of 1.04 ml of DMPU. The reaction mixture is allowed to heat up to room temperature, stirring is continued for a further hour and working up is carried out as usual.

EXAMPLES 9 TO 92

The following compounds of the formula I are prepared analogously or in accordance with the above schemes and possibly by subsequent etherification or esterification of the corresponding hydroxy compounds using standard methods.

| Sample | Formula | m | p |
|---|---|---|---|
| (9) | Ia | 7 | 6 |
| (10) | Ia | 7 | 7 |
| (11) | Ia | 7 | 8 |
| (12) | Ia | 7 | 9 |
| (13) | Ia | 7 | 10 |
| (14) | Ia | 7 | 11 |
| (15) | Ia | 7 | 12 |
| (16) | Ia | 8 | 6 |
| (17) | Ia | 8 | 7 |
| (18) | Ia | 8 | 8 |
| (19) | Ia | 8 | 5 |
| (20) | Ia | 8 | 10 |
| (21) | Ia | 8 | 11 |
| (22) | Ia | 8 | 12 |
| (23) | Ia | 9 | 6 |
| (24) | Ia | 9 | 7 |
| (25) | Ia | 9 | 8 |
| (26) | Ia | 9 | 9 |
| (27) | Ia | 9 | 10 |
| (28) | Ia | 9 | 11 |
| (29) | Ia | 9 | 12 |
| (30) | Ia | 10 | 6 |
| (31) | Ia | 10 | 7 |
| (32) | Ia | 10 | 8 |
| (33) | Ia | 10 | 9 |
| (34) | Ia | 10 | 10 |
| (35) | Ia | 10 | 11 |
| (36) | Ia | 10 | 12 |
| (37) | Ia | 11 | 6 |
| (38) | Ia | 11 | 7 |
| (39) | Ia | 11 | 8 |
| (40) | Ia | 11 | 9 |
| (41) | Ia | 11 | 10 |
| (42) | Ia | 11 | 11 |
| (43) | Ia | 11 | 12 |
| (44) | Ia | 12 | 6 |
| (45) | Ia | 12 | 7 |
| (46) | Ia | 12 | 8 |
| (47) | Ia | 12 | 9 |

-continued

| Sample | Formula | m | p |
|---|---|---|---|
| (48) | Ia | 12 | 10 |
| (49) | Ia | 12 | 11 |
| (50) | Ia | 12 | 12 |
| (51) | Ib | 7 | 6 |
| (52) | Ib | 7 | 7 |
| (53) | Ib | 7 | 8 |
| (54) | Ib | 7 | 9 |
| (55) | Ib | 7 | 10 |
| (56) | Ib | 7 | 11 |
| (57) | Ib | 7 | 12 |
| (58) | Ib | 8 | 6 |
| (59) | Ib | 8 | 7 |
| (60) | Ib | 8 | 8 |
| (61) | Ib | 8 | 9 |
| (62) | Ib | 8 | 10 |
| (63) | Ib | 8 | 11 |
| (64) | Ib | 8 | 12 |
| (65) | Ib | 9 | 6 |
| (66) | Ib | 9 | 7 |
| (67) | Ib | 9 | 8 |
| (68) | Ib | 9 | 9 |
| (69) | Ib | 9 | 10 |
| (70) | Ib | 9 | 11 |
| (71) | Ib | 9 | 12 |
| (72) | Ib | 10 | 6 |
| (73) | Ib | 10 | 7 |
| (74) | Ib | 10 | 8 |
| (75) | Ib | 10 | 9 |
| (76) | Ib | 10 | 10 |
| (77) | Ib | 10 | 11 |
| (78) | Ib | 10 | 12 |
| (79) | Ib | 11 | 6 |
| (80) | Ib | 11 | 7 |
| (81) | Ib | 11 | 8 |
| (82) | Ib | 11 | 9 |
| (83) | Ib | 11 | 10 |
| (84) | Ib | 11 | 11 |
| (85) | Ib | 11 | 12 |
| (86) | Ib | 12 | 6 |
| (87) | Ib | 12 | 7 |
| (88) | Ib | 12 | 8 |
| (89) | Ib | 12 | 9 |
| (90) | Ib | 12 | 10 |
| (91) | Ib | 12 | 11 |
| (92) | Ib | 12 | 12 |

The following examples relate to ferroelectric liquid-crystalline media.

EXAMPLE A

A liquid-crystalline medium is prepared consisting of:
5.8% (2-hexyloxyphenyl)-5-heptylpyrimidine
5.8% (2-octyloxyphenyl)-5-heptylpyrimidine
5.8% (2-decyloxyphenyl)-5-heptylpyrimidine
1.1% (2-p-octyloxyphenyl)-5-octylpyrimidine
1.1% (2-p-nonyloxyphenyl)-5-octylpyrimidine
1.1% (2-p-decyloxyphenyl)-5-octylpyrimidine
7.0% 2-(4-decyloxy-2-fluorophenyl)-5-dodecyloxypyridine
14.1% 2-(4-heptyloxy-2-fluorophenyl)-5-dodecyloxypyridine
14.1% 2-(4-decyloxy-2-fluorophenyl)-5-undecyloxypyridine
5.0% 2-(4-octyloxy-2,3-difluorophenyl)-5-nonylpyrimidine
5.0% 2-(4-heptyloxy-2,3-difluorophenyl)-5-nonylpyrimidine
5.0% 2-(4-nonyloxy-2,3-difluorophenyl)-5-nonylpyrimidine
18.0% 2-(4-hexyloxyphenyl)-5-hexyloxypyrimidine and
10% optically active 2-[4-(2-fluorooctyloxy)-2,3-difluorophenyl]-5-heptylpyrimidine.

This medium has a wide $S_c^*$ range.

EXAMPLE B

A liquid-crystalline medium is prepared consisting of:
5.8% 2-(p-hexyloxyphenyl)-5-heptylpyrimidine
5.8% 2-(p-octyloxyphenyl)-5-heptylpyrimidine
5.8% 2-(p-decyloxyphenyl)-5-heptylpyrimidine
1.1% 2-(p-octyloxyphenyl)-5-octylpyrimidine
1.1% 2-(p-nonyloxyphenyl)-5-octylpyrimidine
2.2% 2-(p-decyloxyphenyl)-5-octylpyrimidine
5.0% 2-(4-decyloxy-2-fluorophenyl)-5-dodecyloxypyridine
10.1% 2-(4-heptyloxy-2-fluorophenyl)-5-dodecyloxypyridine
10.1% 2-(4-decyloxy-2-fluorophenyl)-5-undecyloxypyridine
10% 2-(4-octyloxy-2,3-difluorophenyl)-5-heptylpyridine
5% 2-(4-octyloxy-2,3-difluorophenyl)-5-nonylpyrimidine
5% 2-(4-heptyloxy-2,3-difluorophenyl)-5-nonylpyrimidine
5% 2-(4-nonyloxy-2,3-difluorophenyl)-5-nonylpyrimidine
18% 2-(p-hexyloxyphenyl)-5-hexyloxypyrimidine and
10% optically active 2-[4-(2-fluorooctyloxy)-2-fluorophenyl]-5-heptyloxypyridine.

This medium has an $S_c^*$ phase range of over 60° C. and a high spontaneous polarization.

EXAMPLE C

A liquid-crystalline medium is prepared consisting of:
5.8% 2-(p-hexyloxyphenyl)-5-heptylpyrimidine
5.8% 2-(p-octyloxyphenyl)-5-heptylpyrimidine
5.8% 2-(p-decyloxyphenyl)-5-heptylpyrimidine
1.1% 2-(p-octyloxyphenyl)-5-octylpyrimidine
1.1% 2-(p-nonyloxyphenyl)-5-octylpyrimidine
2.2% 2-(p-decyloxyphenyl)-5-octylpyrimidine
5.0% 2-(4-decyloxy-2-fluorophenyl)-5-dodecyloxypyridine
10.1% 2-(4-heptyloxy-2-fluorophenyl)-5-dodecyloxypyridine
10.1% 2-(4-decyloxy-2-fluorophenyl)-5-undecyloxypyridine
10% 2-(4-octyloxy-2,3-difluorophenyl)-5-heptylpyridine
5% 2-(4-octyloxy-2,3-difluorophenyl)-5-nonylpyrimidine
5% 2-(4-heptyloxy-2,3-difluorophenyl)-5-nonylpyrimidine
5% 2-(4-nonyloxy-2,3-difluorophenyl)-5-nonylpyrimidine
18% 2-(p-hexyloxyphenyl)-5-hexyloxypyrimidine and
10% optically active 2-(4-octyloxy-2-fluorophenyl)-5-(1-cyanoethoxy)pyridine.

This medium has an $S_C^*$ phase range of over 50° C. and a high spontaneous polarization.

EXAMPLE D

A liquid-crystalline medium is prepared consisting of:
5.8% 2-(p-hexyloxyphenyl)-5-heptylpyrimidine
5.8% 2-(p-octyloxyphenyl)-5-heptylpyrimidine
5.8% 2-(p-decyloxyphenyl)-5-heptylpyrimidine
1.1% 2-(p-octyloxyphenyl)-5-octylpyrimidine
1.1% 2-(p-nonyloxyphenyl)-5-octylpyrimidine
2.2% 2-(p-decyloxyphenyl)-5-octylpyrimidine 5.0% 2-(4-decyloxy-2-fluorophenyl)-5-dodecyloxypyrimidine
10.1% 2-(4-heptyloxy-2-fluorophenyl)-5-dodecyloxypyrimidine
10.1% 2-(4-decyloxy-2-fluorophenyl)-5-undecyloxypyrimidine
5.0% 2-(4-octyloxy-2-fluorophenyl)-5-dodecyloxypyridine
10% 2-(4-octyloxy-2,3-difluorophenyl)-5-heptylpyridine
5% 2-(4-octyloxy-2,3-difluorophenyl)-5-nonylpyridine
5% 2-(4-heptyloxy-2,3-difluorophenyl)-5-nonylpyrimidine
18% 2-(p-hexyloxyphenyl)-5-hexyloxypyrimidine and
10% optically active 2-[4-(2-fluorooctyloxy)-2-fluorophenyl]-5-heptyloxypyridine.

This medium has a wide $S_c^*$ phase range and a high spontaneous polarization.

EXAMPLE E

A liquid-crystalline medium is prepared consisting of:
5.8% 2-(p-hexyloxyphenyl)-5-heptylpyrimidine
5.8% 2-(p-octyloxyphenyl)-5-heptylpyrimidine
5.8% 2-(p-decyloxyphenyl)-5-heptylpyrimidine
1.1% 2-(p-octyloxyphenyl)-5-octylpyrimidine
1.1% 2-(p-nonyloxyphenyl)-5-octylpyrimidine
2.2% 2-(p-decyloxyphenyl)-5-octylpyrimidine
5.0% 2-(4-decyloxy-2-fluorophenyl)-5-dodecyloxypyridine
10.1% 2-(4-heptyloxy-2-fluorophenyl)-5-dodecyloxypyridine
10.1% 2-(4-decyloxy-2-fluorophenyl)-5-undecyloxypyridine
5.0% 2-(4-octyloxy-2-fluorophenyl)-5-dodecyloxypyridine
10% 2-(4-octyloxy-2,3-difluorophenyl)-5-heptylpyrimidine
5% 2-(4-octyloxy-2,3-difluorophenyl)-5-nonylpyrimidine
5% 2-(4-nonyloxy-2,3-difluorophenyl)-5-nonylpyrimidine
18% 2-(p-hexyloxyphenyl)-5-hexyloxypyridine and
18% optically active 2-[4-(2-fluorooctyloxy)-2-fluorophenyl]-5-heptyloxypyrimidine and
2% optically active 2-[4-(2-fluorooctyloxy)-2,3-difluorophenyl]-5-heptylpyrimidine.

This medium has a wide $S_c^*$ phase range and a high spontaneous polarization.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A fluorophenylpyridine of the formula I:

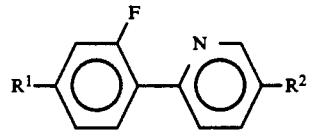

where
R[1] and R[2] are, in each case independently of each other, linear $C_{1-18}$-alkyl or linear $C_{2-5}$-alkenyl radicals, wherein in each case one or more $CH_2$ groups may optionally be replaced by —O—, —CO—O—, —O—CO—or —C≡C—, two oxygen atoms not being adjacent.

2. A fluorophenylpyridine according to claim 1 of the formulae Ia and Ib:

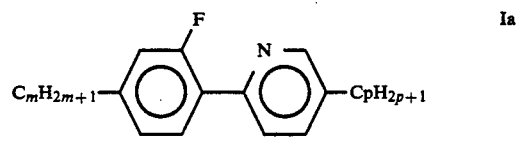

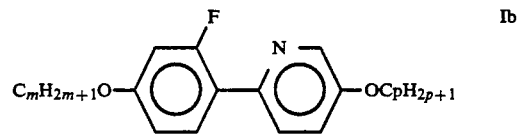

in which
m and p are, in each case independently of each other, 1-18.

3. A fluorophenylpyridine according to claim 1 of the following formula

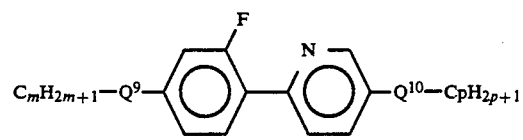

with

| m | Q⁹ | Q¹⁰ | p |
|---|----|-----|---|
| 7 | 0 | 0 | 8 |
| 7 | 0 | 0 | 10 |
| 7 | — | 0 | 11 |
| 7 | — | 0 | 12 |
| 8 | 0 | 0 | 8 |
| 8 | 0 | 0 | 9 |
| 8 | — | 0 | 10 |
| 8 | — | 0 | 11 |
| 8 | — | 0 | 12 |
| 10 | — | 0 | 8 |
| 10 | — | 0 | 9 |
| 10 | 0 | 0 | 10 |
| 10 | 0 | 0 | 11 |
| 10 | 0 | 0 | 12 |
| 12 | — | 0 | 8 |
| 12 | — | 0 | 9 |
| 12 | 0 | 0 | 10 |
| 12 | 0 | 0 | 11 |
| 12 | 0 | 0 | 12 |
| 9 | — | 0 | 7 |
| 12 | 0 | 0 | 8 |

4. A fluorophenylpyridine according to claim 1, wherein R[1] is $C_{1-18}$-alkyl, and R[2] is alkoxy having 1–17 C atoms.

* * * * *